United States Patent [19]
Oka et al.

[11] Patent Number: 5,773,010
[45] Date of Patent: Jun. 30, 1998

[54] **LOW MOLECULAR WEIGHT ALLERGEN OBTAINED FROM *DERMATOPHAGOIDES FARINAE***

[75] Inventors: Satoru Oka; Kazuhisa Ono, both of Hiroshima; Seiko Shigeta; Takeshi Wada, both of Hiroshima-ken, all of Japan

[73] Assignees: Fumakilla Limited, Tokyo; Hiroshima University, Hiroshima-ken, both of Japan

[21] Appl. No.: 564,395

[22] Filed: Nov. 29, 1995

Related U.S. Application Data

[62] Division of Ser. No. 283,905, Aug. 4, 1994, Pat. No. 5,496,554, which is a continuation of Ser. No. 480,617, Feb. 15, 1990, abandoned.

[30] Foreign Application Priority Data

Aug. 24, 1989 [JP] Japan .................................... 1-220064

[51] Int. Cl.$^6$ .............................. A61K 39/35; A61B 8/00; C12Q 1/00; G01N 33/53
[52] U.S. Cl. .................................... 424/276.1; 424/275.1; 424/9.81; 435/4; 435/7.1; 435/7.2
[58] Field of Search .................................... 530/300, 412; 424/184.1, 275.1, 276.1, 9.81; 435/4, 7.1, 7.21, 7.92

[56] References Cited

PUBLICATIONS

Nakagawa et al, Int. Archs Allergy Appl. Immunol., 55, pp. 47–53 (1977).
Chapman et al, Clin. Exp. Immunol., 34, pp. 126–136 (1978).
Kabasawa et al, Jpn. J. Exp. Med., 49, pp. 51–57 (1979).
Krilis et al, Naturwissenschaften, 66, pp. 475–476 (1979).
Stewart et al, Aus. J. Exp. Biol. Med. Sci., 58, pp. 259–274 (1980).
Chapman et al, J. Immunol., 125, pp. 587–592 (1980).
Le Mao et al, Immunology, 44, pp. 239–247 (1981).
Stewart, Int. Archs Allergy Appl. Immun., 69, pp. 224–230 (1982).
Dandeu et al, Immunology, 46, pp. 679–687 (1982).
Krilis et al, J. Allergy Clin. Immunol., 74, pp. 132–141 (1984).
Wahn et al, Allergy, 40, pp. 389–394 (1985).
Lind, J. Allergy Clin. Immunol., 76, pp. 753–761 (1985).
Haida et al, J. Allergy Clin. Immunol., 75, pp. 686–692 (1985).
Lind, Int. Archs Allergy Appl. Immunol., 79, pp. 60–65 (1986).
Mellbye et al, J. Chromatography, 367, pp. 247–253 (1986).
Yasueda et al, Int. Archs Allergy Appl. Immunol., 81, pp. 214–223 (1986).
Heymann et al, J. Immunol., 137, pp. 2841–2847 (1986).
Holck et al, Allergy, 41, pp. 408–417 (1986).
Koda et al, J. Pharmacobio–Dyn., 10, pp. 104–111 (1987).
The Annual Meeting of the Japan Society of Agricultural Chemistry, 62, p. 411 (1988).
The Annual Meeting of the Japan Society of Agricultural Chemistry, 63, pp. 280–281 (1989).
Andersen, A., 1989, Int. Arch. Allery Appl. Immunol. 89:17–23.
Lin et al., Annal. Allergy 67:63–69.

*Primary Examiner*—Laurie Scheiner
*Assistant Examiner*—Jeffrey S. Parkin
*Attorney, Agent, or Firm*—Birch, Stewart, Kolasch & Birch, LLP

[57] ABSTRACT

New purified mite allergens useful as pharmaceutical and diagnostic compositions for the treatment and diagnosis of mite allergic diseases are provided. Both allergens are contained in fecal extracts of mites in culture. The high molecular weight allergen has a weight average molecular weight of 70,000 to 80,000 as determined by sedimentation equilibrium. This is a glycoprotein containing more than about 70% sugar, and possesses allergen activity. The low molecular weight antigen has a molecular weight of 1,500 to 5,000 as determined by Sephadex G25 gel filtration. This is a glycoprotein containing more than about 40% sugar, and also possesses allergen activity.

10 Claims, 12 Drawing Sheets

LOW MOLECULAR WEIGHT ALLERGEN OBTAINED FROM *DERMATOPHAGOIDES FARINAE*

This application is a Divisional of application Ser. No. 08/283,905 filed on Aug. 4, 1994, now U.S. Pat. No. 5,496,554, which is a continuation of application Ser. No. 07/480,617 filed on Feb. 15, 1990, now abandoned.

BACKGROUND OF THE INVENTION

1. Field of the Invention

The present invention relates to a purified mite allergen possessing allergen activity and more specifically to a new glycoprotein possessing allergen activity contained in fecal extracts of mites in culture.

2. Description of the Prior Art

House dust mites are important as a major causative factor of allergic diseases such as atopic bronchial asthma. Traditionally, hyposensitization therapy has been the most important radical therapy for allergic diseases, in which patients are hyposensitized by administration of allergen, the substance which causes allergy. Specifically, in diseases in which antigen identification is easy, such as pollinosis and insect allergy, hyposensitization therapy can be said to have already been highly valued. This therapy, however, necessitates administration of a safe therapeutic antigen because it involves a risk of anaphylaxis due to allergen.

Two mite species, namely *Dermatophagoides pteronyssinus* and *Dermatophagoides farinae*, are reported to play a major role as house dust mite allergens in mite allergic diseases [Allerg. Asthmaforsh: 10, 329–334 (1964), J. Allergy: 42, 14–28 (1968)]. The major mite allergens which have so far been reported include glycoproteins with a molecular weight of 24 to 28 kD (pI 4.6 to 7.2) and/or proteins with a molecular weight of 14.5 to 20 kD (pI 5 to 8.3), both contained in mite feces and/or mite bodies [e.g. J. Immunol.: 125, 587–592(1980)/J. Allergy Clin. Immunol.: 76, 753–761(1985)/Immunology: 46, 679–687(1982)/Int. Arch. Allergy Appl. Immunol.: 81, 214–223(1986)/J. Allergy Clin. Immunol.: 75, 686–692(1985)].

On the other hand, the present inventors reported the presence of components which exhibit specific reactivity to serum IgG of mite asthma patients and which induce leukocyte histamine release in mite asthma patients in fractions with higher molecular weight and those with lower molecular weight in comparison with the above-mentioned major mite allergens [The Annual Meeting of the Japan Society of Agricultural Chemistry: 62, 411(1988)]. These components, however, remained to be purified to a degree such that they can be used as antigens for hyposensitization therapy.

Mite allergic diseases have been diagnosed mainly on the basis of inquiry in combination with skin reaction test using a house dust extract and/or mite body extract in most cases, with measurements of serum IgE antibody titer (relative values) taken by the RAST method used in only a very few cases; it has been considerably difficult to make direct diagnoses of mite allergic diseases.

Traditionally, house dust extract solutions have been used for hyposensitization therapy for bronchial asthma involving house dust mites as specific antigens; however, their dose is subject to extreme limitation and their therapeutic effect is extremely low, since they are very indefinite in chemical structure and contain a wide variety of impurity substances which may induce anaphylaxis. Therefore, from the viewpoint of efficacy and safety, it is desired that a valuable antigen for hyposensitization therapy will be developed.

Also, it is important to make quick and accurate diagnoses of mite allergic diseases in appropriate treatment of mite allergic diseases; a new diagnostic system is expected to be well established.

SUMMARY OF THE INVENTION

The object of the present invention is to provide a new purified mite allergen which is very valuable for use as a remedy and a diagnostic drug.

Accordingly, it is an object of the present invention to provide a new purified mite allergen possessing allergen activity which can be extracted from fecal extracts of mites in culture.

It is a further object of the present invention to provide a method of producing said new purified mite allergen.

It is another object of the present invention to provide a new remedy for mite allergic diseases.

It is yet a further object of this invention to provide a new diagnostic drug for mite allergic diseases.

With the aim of accomplishing these objects, the present inventors made intensive investigations of allergens contained in culture extracts of *Dermatophagoides farinae* with mite bodies removed, and found that a glycoprotein with a molecular weight of 70,000 to 80,000, and that with a molecular weight of 1,500 to 5,000, possess potent allergen activity. The present inventors made further investgations based on this finding, then developing the present invention.

Accordingly, the present invention comprises purified allergens possessing the following physicochemical and biological properties:

i) High molecular weight purified mite allergen:
 ① being contained in fecal extracts of mites in culture;
 ② glycoprotein containing more than about 70% sugar.
 ③ a weight-average molecular weight: 70,000 to 80,000 (as determined by the sedimentation equilibrium method)
 ④ possessing allergen activity.

ii) Low molecular weight purified mite allergen:
 ① being contained in fecal extracts of mites in culture;
 ② glycoprotein containing more than about 40% sugar;
 ③ a molecular weight: 1,500 to 5,000 (as determined by the Sephadex G25 gel filtration method)
 ④ possessing allergen activity.

The present invention also comprises a method of producing the above-mentioned mite allergens, characterized by extraction of feces of mites in culture with a saturated sodium chloride solution and/or a buffer with a moderate ionic strength and subsequent fractionation of the obtained extract by gel filtration and other techniques.

The present invention further comprises a remedy for mite allergic diseases and a diagnostic drug for mite allergic diseases, both containing the above-mentioned mite allergen as active ingredient.

DESCRIPTION OF THE PREFERRED EMBODIMENT

Figure 1:
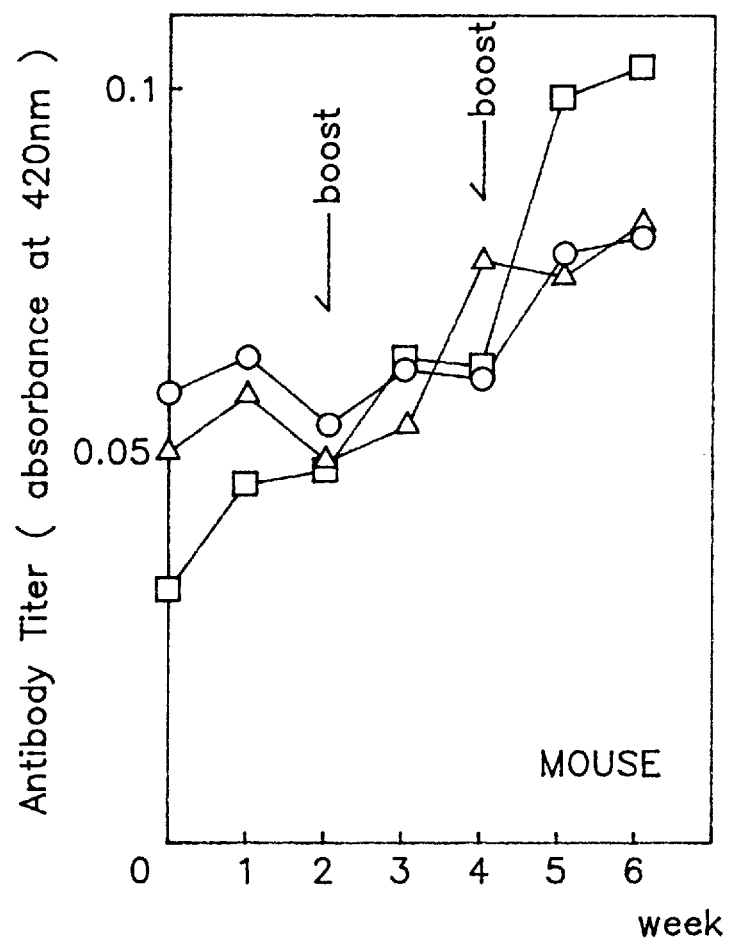
FIG. 1 shows changes in antibody titer in mice immunized with Dff-1-2-0.1A.

In the present specification, amino acids, etc. are sometimes represented by abbreviations based on the IUPAC-IUB Nomenclature and those which are commonly used in relevant fields. Their examples are given below.

Abbreviations for amino acid residues are as follows:

Asx aspartic acid and/or asparagine
Thr threonine
Ser serine
Glx glutamic acid and/or glutamine
Gly glycine
Ala alanine
Val valine
Ile isoleucine
Leu leucine
Tyr tyrosine
Phe phenylalanine
His histidine
Lys lysine
Arg arginine
Pro proline
Cys cysteine
Met methionine Abbreviations for sugars are as follows:

HexNAc amino sugar
dHex deoxyhexose
Pen pentose
Hex hexose

It does not matter whether the purified mite allergen of the present invention comprises a single purified mite allergen or a number of purified mite allergens (i.e., in the form of a mixture of purified mite allergens), as long as it meets the above-mentioned requirements ①  through ④.

Some representative examples of the purified mite allergen of the present invention are hereinafter described in more detail.

i) High molecular weight purified mite allergen (Dff-1-2-0.1A)

(1) Color and appearance: White (lyophilized product)
(2) Water solubility: Freely soluble
(3) Molecular weight: The weight-average molecular weight is about 74,000 as determined by the sedimentation equilibrium method.
(4) Specific volume: 0.6076 (as determined by the density gradient tube method)
(5) Sedimentation coefficient: $S_{20,w}$=2.1495
(6) Composition: Sugar is contained at 77% as determined by compositional analysis.

Amino acid composition

200 μl of a 0.2% sample solution was mixed with 200 μl of 12N HCl and hydrolyzed at 110° C. in a sealed $N_2$-saturated test tube for 24 hours. After evaporating the hydrolysate to dryness, a small amount of water was added, and this was followed by re-evaporation to dryness. This procedure was repeated in three cycles to remove the hydrochloric acid. The resulting dry product was dissolved in 1 ml of a dilution buffer for amino acid analysis. This solution was then assayed using an amino acid analyzer (produced by Beckman Co.).

Sugar composition

Total neutral sugar was quantitatively determined by the phenol sulfuric acid method using glucose as reference substance.

Each neutral sugar and amino sugar was quantitatively determined by the GLC method after the sample was hydrolyzed at 100° C. in 4N TFA (trifluoroacetic acid) for 4 hours, reduced with $NaBH_4$, and then acetylated by heating at 100° C. for 4 hours in the presence of acetic anhydride.

Asx 23.9
Thr 40.7
Ser 27.1
Glx 49.3
Gly 16.1
Ala 13.3
Val 9.5
Ile 8.4
Leu 11.3
Tyr 1.5
Phe 5.7
His 3.5
Lys 5.3
Arg 1.8
Pro 15.9
Pen 412.8
Hex 354.5 (μg/mg)

(7) Possesses allergen activity.

To be judged on the basis of skin reactivity in mite allergy patients and results of a patient leukocyte histamine release test using HPLC.

(8) Does not induce anaphylactic reaction.

Guinea pigs immunized by a standard method are observed for anaphylactic reaction at the time of booster immunization.

ii) Low molecular weight purified mite allergens (LM-ch)

(1) Color and appearance: White to light brown (lyophilized product)
(2) Water solubility: Freely soluble
(3) Molecular weight: 1,500 to 5,000 as determined by the gel filtration method using Sephadex G25.
(4) Composition: a sugar content of 55% as determined by compositional analysis and a sugar content of about 41% as determined by the phenol sulfuric acid method.

Asx 67.2
Thr 28.2
Ser 32.0
Glx 113.1
Gly 85.3
Ala 32.3
Cys 2.2
Val 17.2
Ile 9.9
Leu 11.9

Tyr 0.9
Phe 4.7
His 5.4
Arg 16.6
Lys 20.8
HexNAc 64.3
dHex 17.2
pen 252.2
Hex 216.4 (μg/mg)

(5) Possesses allergen activity.

To be judged on the basis of skin reactivity mite allergy patients and results of a patient leukocyte histamine release test using HPLC.

(6) Does not induce anaphylactic reaction.

Guinea pigs immunized by a standard method are observed for anaphylactic reaction at the time of booster immunization.

Method of production

Examples of the production method for the purified mite allergen of the present invention include the following:

a) Preparation of crude mite fecal antigen

Any of *Dermatophagoides farinae* and *Dermatophagoides pteronyssinus* can be used as the starting material for the production of mite antigen. These mites are cultured on mite culture medium; the resulting culture broth is subjected to extraction treatment.

For extraction treatment, a saturated sodium chloride solution and/or a phosphate buffer is added to the culture broth, and this is followed by stirring. After being kept standing at room temperature for 30 minutes, the mixture is centrifuged at 3000 rpm for 30 minutes; the resulting supernatant is pooled. In this extraction, any other buffer can be used as extraction solvent, as long as its ionic strength is moderate. Examples of such buffers include lactate buffers, acetate buffers, citrate buffers, Tris-HCl buffers and borate buffers. Mite bodies floating on the surface of the supernatant are removed by filtration. The pooled supernatant is filtered and dialyzed against deionized water; the crude mite fecal extract thus obtained is used as the starting material.

This crude mite fecal extract is then passed through, for example, an ultrafiltration membrane with an exclusion limit of molecular weight 10,000 (UF-20CS-10 PS) to fractionate it into a high molecular weight crude mite fecal antigen, which does not pass through this membrane, and a low molecular weight crude mite fecal antigen, which passes through the membrane.

b) Purification of crude mite fecal antigen

The crude mite fecal antigen can be purified by known ordinary methods of protein purification such as gel filtration chromatography, ultrafiltration, ion exchange chromatography, affinity chromatography, hydrophobic chromatography, isoelectric focusing and gel electrophoresis. These methods can be used singly or in combination. In this purification process, the elution pattern is monitored by:

(i) assay of the antigeneic activity of each fraction by enzyme-linked immunosorbent assay (ELISA) of reactivities to mite asthma patient serum specific IgE and IgG, rabbit anti-high molecular weight mite fecal serum, rabbit anti-high molecular weight mite fecal antibody, fecal antigen-specific mouse monoclonal antibody, etc. [Immunochemistry, 8, 871–874 (1971)], (ii) assay of the antigenic activity of each fraction by radioimmunoassay using rabbit anti-high molecular weight mite fecal serum, (iii) assay of the allergen activity of each fraction on the basis of skin reaction activity, (iv) assay of the allergen activity of each fraction on the basis of mite allergy patient leukocyte histamine release activity, and other means. For example, the following methods can be used:

(i) Purification of high molecular crude mite fecal antigen

The high molecular weight crude mite fecal antigen is subjected to gel filtration on Ultrogel AcA54 (produced by LKB Co.). The elution pattern is monitored on the basis of reactivities (ELISA) to mite asthma patient serum specific IgG and to rabbit anti-high molecular weight mite fecal antibody and patient leukocyte histamie release capability; fractionation is performed while using protein content and absorbance at 280 nm as guide parameters.

The fraction which shows strong reactivity in ELISA using patient serum specific IgG, rabbit anti-high molecular weight mite fecal antibody and mouse monoclonal antibody and which showed strong leukocyte histamine release capability and strong skin reaction activity is further fractionated on Sepharose 6B (produced by Pharmacia Fine Chemical Co.) and then on DEAE-Toyopearl (produced by Tosoh Corporation) to purify a fraction with antigen activity.

(ii) Purification of low molecular weight crude mite fecal antigen

The low molecular weight crude mite fecal antigen is subjected to gel filtration using Sephadex G25 (produced by Pharmacia Fine Chemical Co.). The elution pattern is monitored on the basis of mite asthma patient leukocyte histamine release capability and ELISA-assayed reactivities to patient serum specific IgE and rabbit anti-high molecular weight mite fecal serum, and fractionation is performed while using protein content and absorbance at 280 nm as guide parameters.

The fraction which showed strong skin reaction activity is further subjected to gel filtration on Ultrogel AcA54 (produced by LKB Co.) to purify a fraction with antigen activity.

Another combination is also efficient in which fractionation on Ultrogel AcA54 is first conducted, and the obtained low molecular fraction is further subjected to gel filtration on Sephadex G25.

Application as remedy for mite allergic diseases

The purified mite allergen of the present invention is valuable as a remedy for hyposensitization therapy for mite allergic diseases.

Here, mite allergic diseases involve all allergic diseases that are caused by mite specific antigens, such as atopic bronchial asthma, allergic rhinitis, allergic conjunctivitis and atopic dermatitis.

The purified mite allergen obtained by the above-mentioned method is concentrated and then collected in the form of a solution or syrup, or is concentrated, dried and then collected in the form of powder; it is then used as a remedy for hyposensitization therapy for mite allergic diseases. The remedy for hyposensitization therapy for mite allergic diseases can be used as it is, or it can be used in formulation with ordinary adjuvants and various additives such as stabilizers, excipients, dissolution aids, emulsifiers, buffers, analgesics, preservatives and colorants as necessary.

The remedy for hyposensitization therapy for mite allergic diseases can be administered via ordinary routes of administration such as, intracutaneous, subcutaneous, intramuscular and intraperitoneal injection.

The remedy for hyposensitization therapy for mite allergic diseases can also be used in the form of a percutaneous or permucosal agent such as a troche, a sublingual tablet, an ophthalmic solution, an intranasal spray, a poultice, a cream, or a lotion. It is administered at an appropriate dose and administration frequency chosen according to the route of administration, symptoms and other aspects so that the dose per adult in each administration is less than about 20 μg once a week.

Also, the remedy for hyposensitization therapy is valuable not only as a remedy but also as a preventive drug for mite allergic diseases. The remedy for hyposensitization therapy can be used safely in humans since it does not induce an anaphylactic reaction.

Application as diagnostic drug for mite allergic diseases

The purified mite allergen of the present invention is valuable as a diagnostic drug for mite allergic diseases.

Accordingly, the purified mite allergen is used as a titration reagent to titrate each of a given amount of patient blood and a given amount of a blood cell suspension prepared by suspending in a buffer a blood cell fraction obtained by centrifugation of patient blood, followed by assay of the amount of histamine released from basophils (a type of leukocyte) in response to allergen stimulation [Journal of Japanese Society of Allergology: 33, 692 (1984) /Journal of Japanese Society of Allergology: 33, 733 (1984)].

In this histamine release titration, assay is made of the amount of histamine released at a point corresponding to 50% of the maximum release amount (inflexion point of the titration curve). In this titration:
(i) the allergen sensitivity of the patient is determined directly from the titration value of the blood cell suspension, and
(ii) the titration value of blood is normally higher than that of the blood cell suspension because an IgG antibody (blocking antibody) capable of allergen neutralization is present in blood plasma.

Therefore, the blocking antibody titer can be determined from the size of the shift of the blood titration curve from the blood cell suspension titration curve. As shown in Table 1, it is possible to make accurate diagnoses of mite allergy on the basis of sensitivity and this blocking antibody titer. The purified mite allergen is also valuable in monitoring the hyposensitization therapeutic effect.

TABLE 1

| | Sensitivity | Blocking antibody |
|---|---|---|
| 1. Patients with mite allergy | positive | negative |
| 2. Patients with mite allergy successful in the hyposensitization therapy | positive | positive |
| 3. Healthy man possessing IgE antibody (naturally hyposensitized) | positive | positive |
| 4. Healthy man | negative | negative |

Allergen activity tests and anaphylaxis induction tests

The following experiments revealed that the purified mite allergen of the present invention possesses allergen activity and is free of any anaphylaxis induction property.

Experiment 1

100 μg of Dff-1-2-0.1A in conjunction with Freund's complete adjuvant (produced by Difco Laboratories) was intraperitoneally injected into three BALB/c mice (4 weeks in age) for the first immunization at 0 week. Booster immunization was conducted at 2 and 4 weeks following the first immunization.

As shown in FIG. 1, the anti-Dff-1-2-0.1A antibody titer in mouse serum showed a clear increase; sufficient immunogenicity was found. Based on this finding, it was judged that Dff-1-2-0.1A is capable of blocking antibody induction and can be thus used as a therapeutic antigen.

Experiment 2

Figure 2:
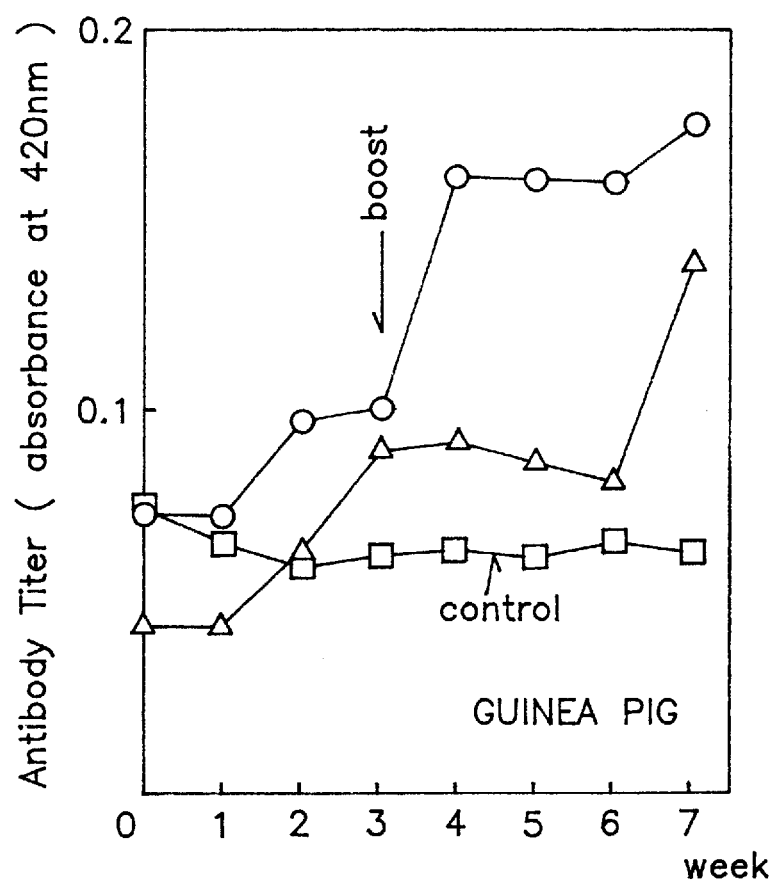
FIG. 2 shows changes in antibody titer in guinea pigs immunized with Dff-1-2-0.1A.

1 mg of an eluate of Dff-1-2-0.1A in conjunction with alum was intraperitoneally injected into two guinea pigs for the first immunization at 0 week. Booster immunization was conducted at 3 weeks following the first immunization. For control, a physiological saline in conjuction with alum was intraperitoneally injected into one guinea pig in the same manner as above. As shown in FIG. 2, the anti-Dff-1-2-0.1A antibody titer in guinea pig serum showed a clear increase; sufficient immunogenicity was found. However, no anaphylactic symptoms were noted in the observation immediately after booster immunization at 3 weeks. Based on this finding, Dff-1-2-0.1A was judged to be free of any anaphylaxis induction property.

Experiment 3

Dff-1-2-0.1A was tested for allergen activity by a skin reaction test in mite allergen patients, which was conducted as follows:

The sample was diluted with 0.9% NaCl in a 0.5% phenol solution to a concentration of 0.0005%. This dilute solution, in an amount of 20 μl, was intracutaneously injected to mite allergy patients at the flexion side of the forearm by means of an injector for tuberculin. The longer and shorter diameters of the erythemata and wheals were measured about 15 minutes after injection; their average value was used for activity assay. The criteria of activity assay are shown in Table 2.

TABLE 2

| Diameter of erythemata (mm) | Criteria |
|---|---|
| 9> | – |
| 10–19 | ± |
| 20–29 | + |
| 30–39 | ++ |
| >40 | +++ |

(Note that when the diameter of wheals exceeded 8 mm, the patient was judged to be positive (+) for allergen activity even when the diameter of erythemata was not more than 19 mm.)

As shown in Table 3, Dff-1-2-0.1A showed allergen activity but it did not induce any anaphylactic reaction.

TABLE 3

| Patient | Dff-1-2 | −0.1A | −0.1B | −0.3A | −0.3B |
|---|---|---|---|---|---|
| 1 | + | + | ± | ± | − |
| 2 | − | − | ± | ± | − |
| 3 | + | + | + | + | + |
| 4 | ++ | ++ | − | − | − |
| 5 | − | +++ | − | − | − |

Experiment 4

LM-1A, LM-1B, LM-2A and LM-2B were tested for allergen activity by a skin reaction test in mite allergy patients, which was conducted in the same manner as in Experiment 3.

As shown in Table 4, LM-1A, LM-1B and LM-2B showed allergen activity, but anaphylactic reaction was not induced as in Experiment 2 and 3.

TABLE 4

| Patient | LM-1A | LM-1B |
|---|---|---|
| 21 | + | + |
| 22 | ++ | +++ |
| 23 | ± | ++ |
| 24 | ++ | + |
| 25 | − | + |

TABLE 4-continued

| Patient | LM-2A | LM-2B |
|---|---|---|
| 26 | − | − |
| 27 | − | − |
| 28 | − | ± |
| 29 | − | − |
| 30 | − | − |
| 31 | − | + |
| 32 | − | ++ |
| 33 | − | ++ |
| 34 | − | + |
| 35 | − | − |
| 36 | − | − |
| 37 | − | − |

Experiment 5

The allergen activities of LM-1A, LM-1B, LM-2A and LM-2B were assayed by a mite allergy patient leukocyte histamine release test.

Figure 3A:
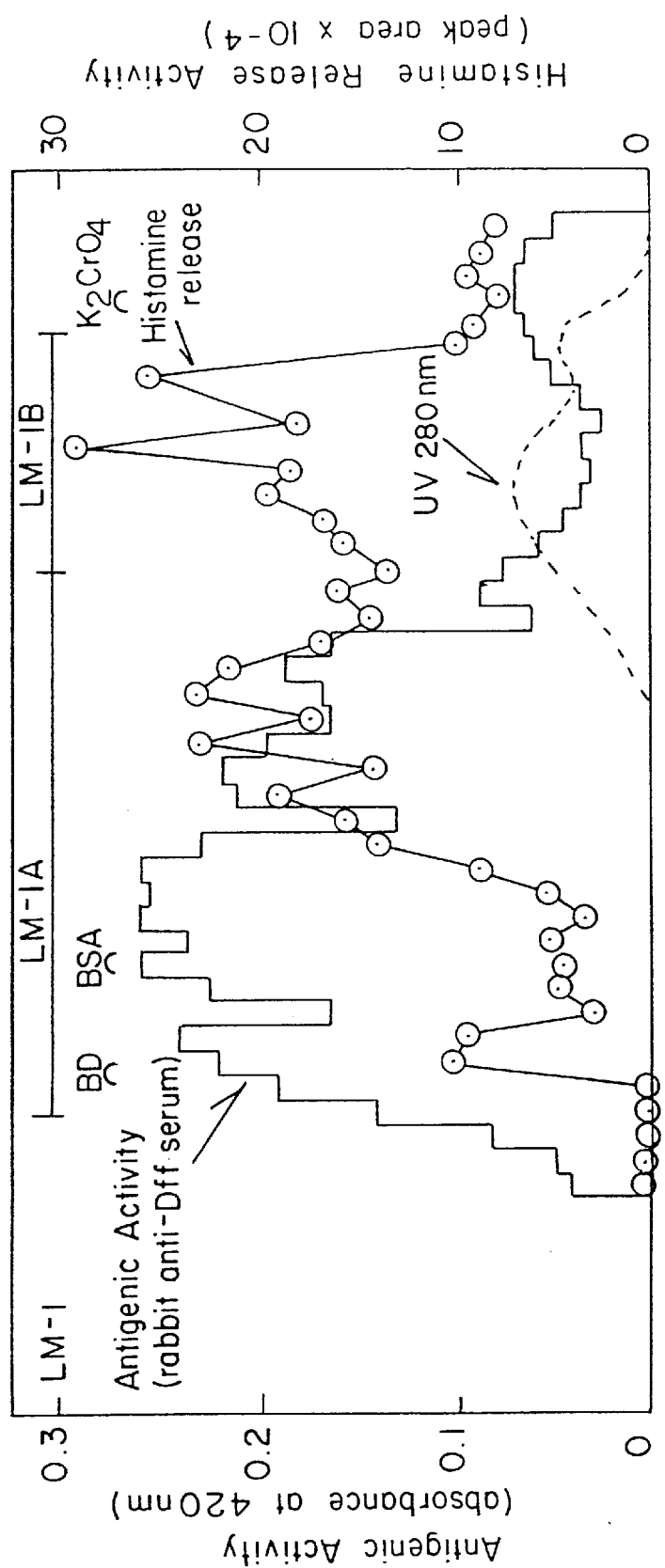
FIG. 3 shows results of gel filtration of LM-1 and LM-2 on Ultrogel AcA54.
Figure 3B:
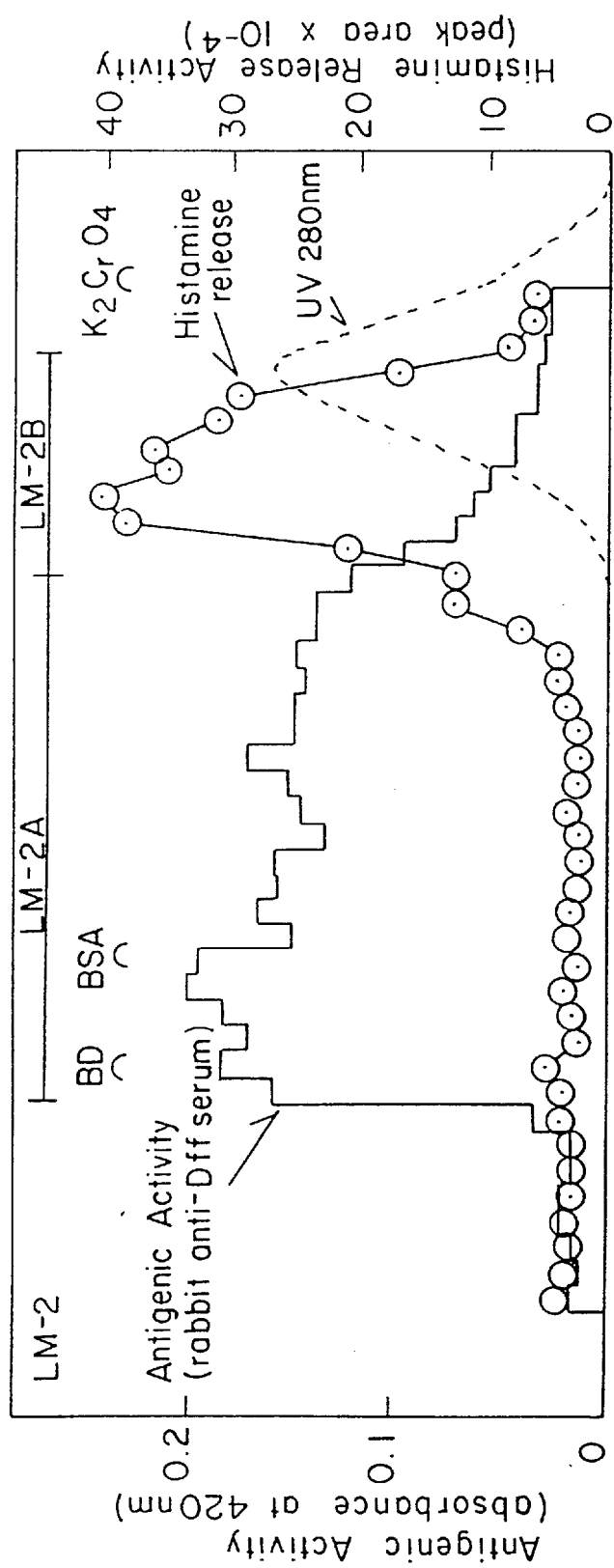

The leukocyte histamine release test was conducted in accordance with a known method [Allergy: 33, 692 (1984)]. Accordingly, the reaction between each fraction sample and basophil surface IgE in mite allergy patient serum was tested by measuring histamine by HPLC (high performance liquid chromatography). As shown in FIG. 3, histamine release activity was found in the LM-1A, LM-1B and LM-2B fractions.

EXAMPLES

The present invention is hereinafter described in more detail by means of the following examples, but the present invention is not by any means limited by these examples.

Example 1

Preparation of high molecular crude mite fecal antigen and low molecular crude mite fecal antigen:

*Dermatophagoides farinae* was grown in rat/mouse/hamster food M (produced by Oriental Yeast Co.) at a temperature of 26±2° C. and a humidity of 75% RH until the mite density reached 20000 to 30000 mites/gram medium. This was followed by addition of a saturated sodium chloride solution at 1 l per 100 g of the mite culture medium, and then agitation. After being kept standing at room temperature for 30 minutes, this mixture was centrifuged at 3000 rpm for 30 minutes. The mite bodies floating on the surface of the supernatant were removed by filtration. A saturated sodium chloride solution was again added to the precipitate, and this was followed by the same procedure as above. To the resulting precipitate was added 1 l of a 10 mM phosphate buffer, and this was followed by the same procedure as with the saturated sodium chloride solution (2 cycles). The extract thus obtained was dialyzed against tap water overnight. This dialyzate was subjected to ultrafiltration of a fractional molecular weight of 10000 (the membrane was UF-20CS-10PS, produced by Tosoh Corporation) to fractionate it into a fraction with a molecular weight of more than 10000 and the other fraction with a molecular weight of less than 10000. Each fraction was concentrated and lyophilized to yield a high molecular weight crude mite fecal antigen and a low molecular weight crude mite fecal antigen.

As a result, 93 g of the high molecular crude mite fecal antigen and 70 g of the low molecular crude mite fecal antigen were obtained from 3.52 kg of mite culture medium.

Example 2

Purification of high molecular crude mite fecal antigen:
(a) Fractionation by gel filtration on Ultrogel AcA54

Fractionation was conducted by adding 30 ml of a 3.3% solution of the high molecular weight crude mite fecal antigen, previously centrifuged to remove the insoluble matter, on Ultrogel AcA54 equilibrated with a 0.9% NaCl solution, while monitoring the UV absorbance at 280 nm. The flow rate was 2 ml/min; samples were taken in an amount of 32 ml for each fraction.

Figure 4:
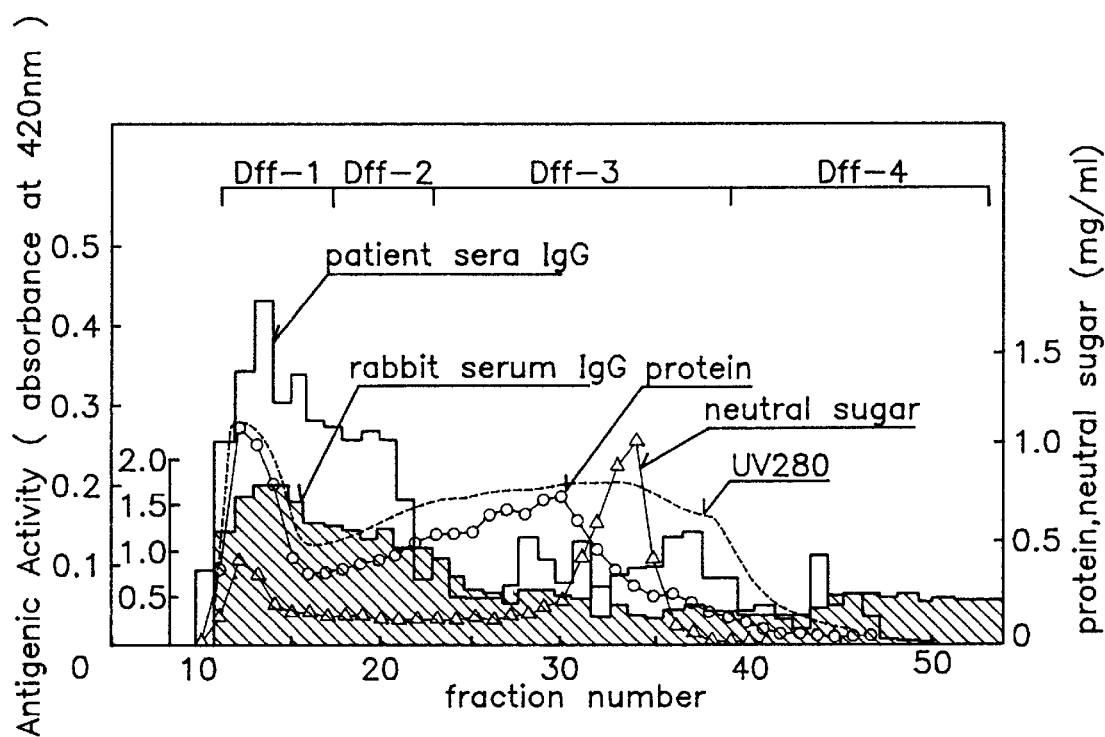
FIG. 4 shows results of gel filtration of a high molecular crude mite fecal antigen on Ultrogel AcA54.

Reactivities to IgG in mite allergy patient serum and to IgG in rabbit anti-high molecular weight crude mite fecal antigen serum, UV absorbance, neutral sugar content as determined by the phenol sulfuric acid method, and protein content (method of Folin-Lowry) were determined for each fraction; as shown in FIG. 4, four fractions, namely Dff-1 through Dff-4, were obtained. These four fractions were examined for skin reaction activity in mite allergy patients; Dff-1, Dff-2 and Dff-3 showed high activity, with an average of ++, while Dff-4 showed almost no activity.

High reactivities to IgG in mite allergy patient serum and to IgG in rabbit anti-high molecular weight crude mite fecal antigen serum were found for Dff-1. Also, the anti-high molecular weight mite fecal antigen-specific monoclonal antibody (MoAb T4) reacted with all fractions. The yield was 228.3 mg of Dff-1 per gram of the high molecular weight crude mite fecal antigen.

(b) Fractionation by gel filtration on Sepharose 6B

Figure 5:
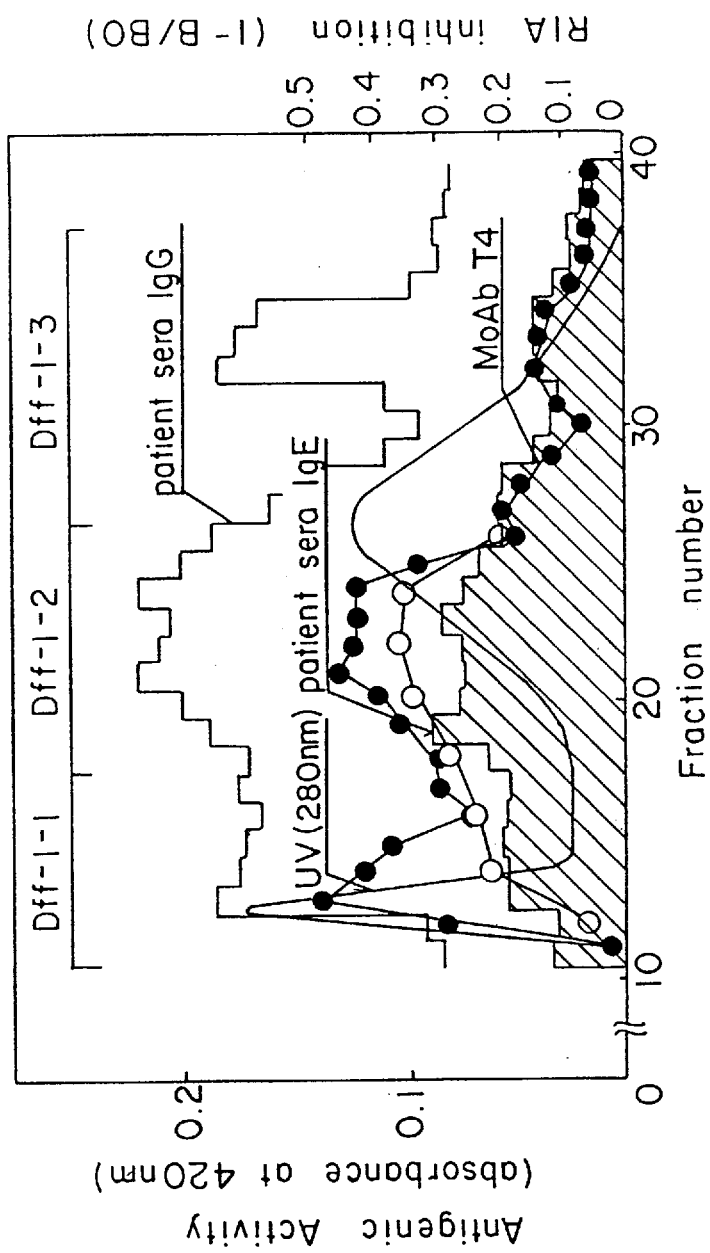
FIG. 5 shows results of gel filtration of Dff-1 on Sepharose 6B.

Dff-1, which showed high activity in fractionation on Ultrogel AcA54 (produced by LKB), was further fractionated on Sepharose 6B (produced by Pharmacia Fine Chemical Co.). The fractions thus obtained were tested for reactivities to patient serum IgG and IgE by the ELISA method; Fraction Nos.18 through 26 showed high activity. Also conducted was radioimmunoassay (RIA). First, $^{125}$I-Dff-1 was purified by affinity chromatography using rabbit anti-high molecular weight crude mite fecal antigen serum-Sepharose CL-4B. The Gly-HCl elution fraction thus obtained was subjected to RIA; high activity was detected in Fraction Nos.18 through 26 as in ELISA. Taking note of these results, Dff-1 was fractionated into three fractions, namely Dff-1-1, Dff-1-2 and Dff-1-3, as shown in FIG. 5. As a result, 130.2 mg of Dff-1-1, 379.1 mg of Dff-1-2 and 158.5 mg of Dff-1-3 were obtained from 1 g of Dff-1. These three fractions were test for skin reaction activity in patients; all fractions showed high activity.

Dif-1-2, which showed high activities in ELISA, RIA and skin reaction, was further purified. The reactivities of the various fractions to MoAb T4 corresponded well with those to patient serum IgG.

(c) Fractionation by ion exchange chromatography on DEAE-Toyopearl (1)

Figure 6:
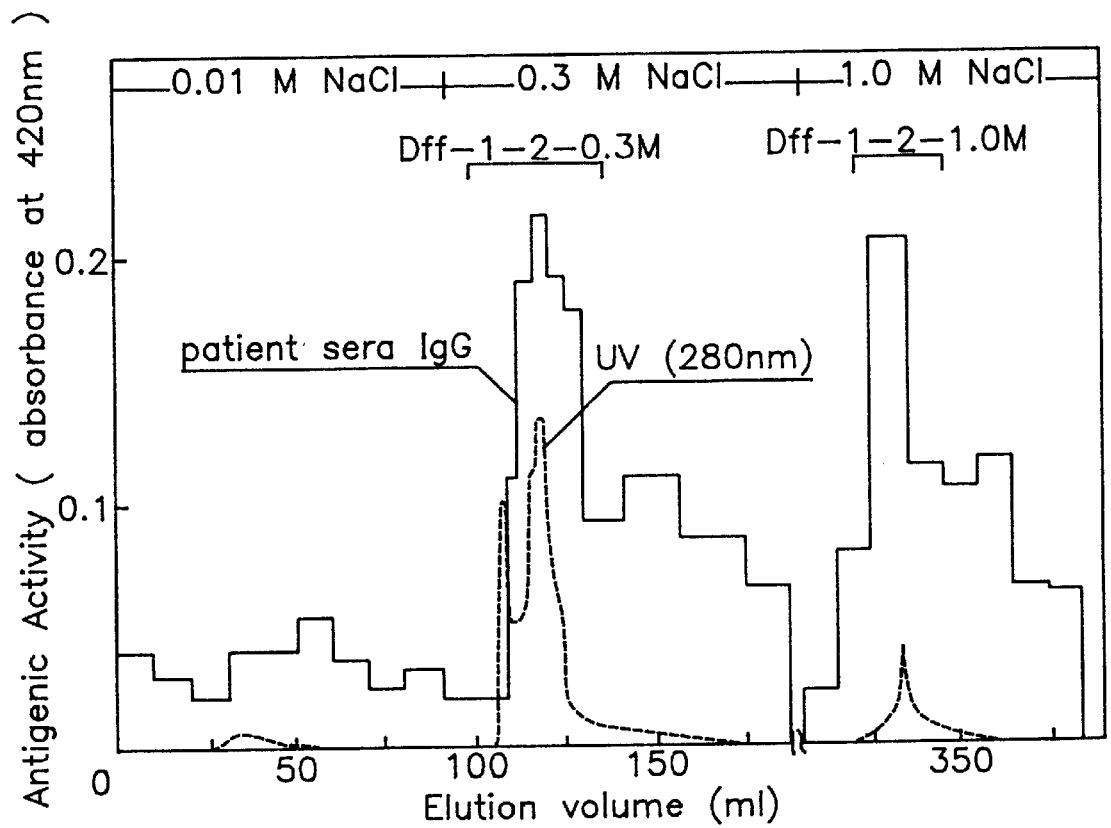
FIG. 6 shows results of ion exchange chromatography of Dff-1-2 on DEAE-Toyopearl.

Since preliminary experimentation revealed that Dff-1-2 is not adsorbed to CM-Toyopearl (produced by Tosoh Corporation) but rather to DEAE-Toyopearl (produced by Tosoh Corporation) at pH 6.0, DEAE-Toyopearl was used for ion exchange chromatography. Since an active component was eluted in elution with 0.3M NaCl in the preliminary experimentation, elution was conducted with 0.3M NaCl; further elution was conducted with 1M NaCl to elute the remaining adsorbed component. The results are shown in FIG. 6. Activity was detected in both eluates with 0.3M NaCl and eluates with 1M NaCl, while almost no activity was present in the effluent. These active fractions were respectively named Dff-1-2-0.3M and Dff-1-2-1.0M, and pooled.

As a result, 34.6 mg of Dff-1-2-0.3M, 4.79 mg of Dff-1-2-1.0M and 7.32 mg of effluent were obtained from 100 mg of Dff-1-2. Assay of skin reaction activity revealed that Dff-1-2-0.3M showed high activity, while Dff-1-2-1.0M showed almost no activity.

(d) Fractionation by ion exchange chromatography on DEAE-Toyopearl (2)

Figure 7:
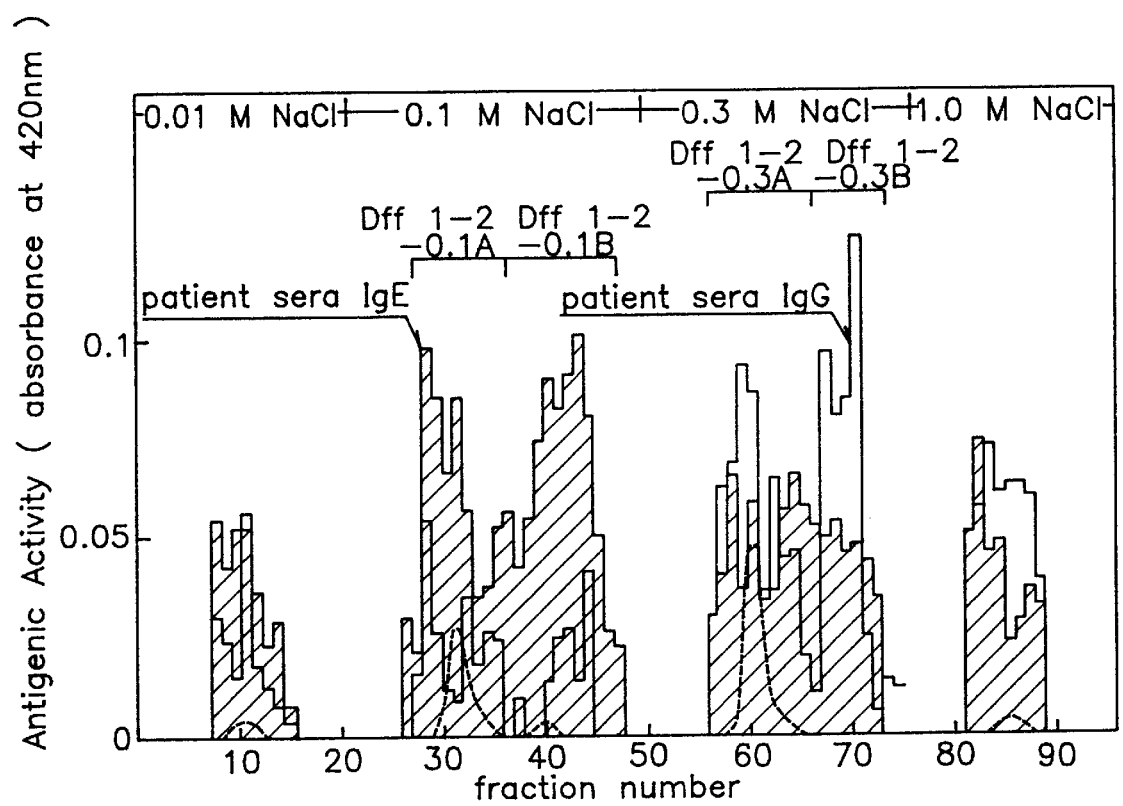
FIG. 7 shows results of ion exchange chromatography of Dff-1-2 on DEAE-Toyopearl.

For the purpose of further fractionation, Dff-1-2-0.3M was subjected to ion exchange chromatography in which elution was conducted in the presence of an NaCl density gradient of 0 to 0.5M. Monitoring of antigenic activity by means of patient serum IgG and MoAb T4 revealed that the reaction peak for patient serum IgG was not identical with that for MoAb T4, and thus at least two immunologically different components are presented. Then, to separate the fraction corresponding to the peak for MoAb T4, stepwise elution was conducted with 0.1M NaCl and 0.3M NaCl. Monitoring by means of patient serum IgG and MoAb T4 revealed that MoAb T4 showed high reactivity mainly to the 0.1M elution fraction, while patient serum IgG showed high reactivity mainly to the 0.3M elution fraction. The same fractions were used to determine reactivity to patient serum IgE; patient serum IgE showed high reactivity to the 0.1M elution fraction as in the case of MoAb T4 as shown in FIG. 7. Based on this finding, the four ELISA peaks were respectively named Dff-1-2-0.1A, Dff-1-2-0.1B, Dff-1-2-0.3A and Dff-1-2-0.3B and pooled. Note that 7.7 mg of Dff-1-2-0.1A, 3.5 mg of Dff-1-2-0.1B, 7.0 mg of Dff-1-2-0.3A and 2.5 mg of Dff-1-2-0.3B were obtained from 100 mg of Dff-1-2. These four fractions were tested for skin reaction activity. Almost all activity was recovered in Dff-1-2-0.1A, the leading peak obtained in 0.1M NaCl elution.

These four fractions were subjected to compositional analysis (Table 5); the active fraction Dff-1-2-0.1A was found to have a considerable sugar content of 77%.

TABLE 5

| composition | Dff-1-2-0.1A |
| --- | --- |
| Asx | 23.9 |
| Thr | 40.7 |
| Ser | 27.1 |
| Glx | 49.3 |
| Gly | 16.1 |
| Ala | 13.3 |
| Val | 9.5 |
| Ile | 8.4 |
| Leu | 11.3 |
| Tyr | 1.5 |
| Phe | 5.7 |
| His | 3.5 |
| Lys | 5.3 |
| Arg | 1.8 |
| Pro | 15.9 |
| Pen | 412.8 |
| Hex | 354.5 |
| | (μg/mg) |

These four fractions were also subjected to SDS-PAGE using 7.5% acrylamide gel; the active fraction Dff-1-2-0.1A was not stained in Coomassie staining at all. Dff-1-2-0.1A was then subjected to PAS staining; not a band but a relatively wide range was stained red at a position corresponding to a considerably higher molecular weight. This was attributed to the fact that electrophoretic migration was hampered due to high sugar content; therefore, it was impossible to estimate the molecular weight. Thus, the molecular weight was determined via ultracentrifugation. The specific volume was 0.6076; one major peak and one minor peak were detected by the sedimentation velocity method presence of at least two components was thus confirmed. The sedimentation coefficient was $S_{20,w}$=2.1495 for the major component and $S_{20,w}$=5.4044 for the minor component; the average molecular weight was determined to be 74,238 by the sedimentation equilibrium method.

Example 3

Purification of low molecular weight crude mite fecal antigen:
(a) Fractionation by gel filtration on Sephadex G25

Figure 8:
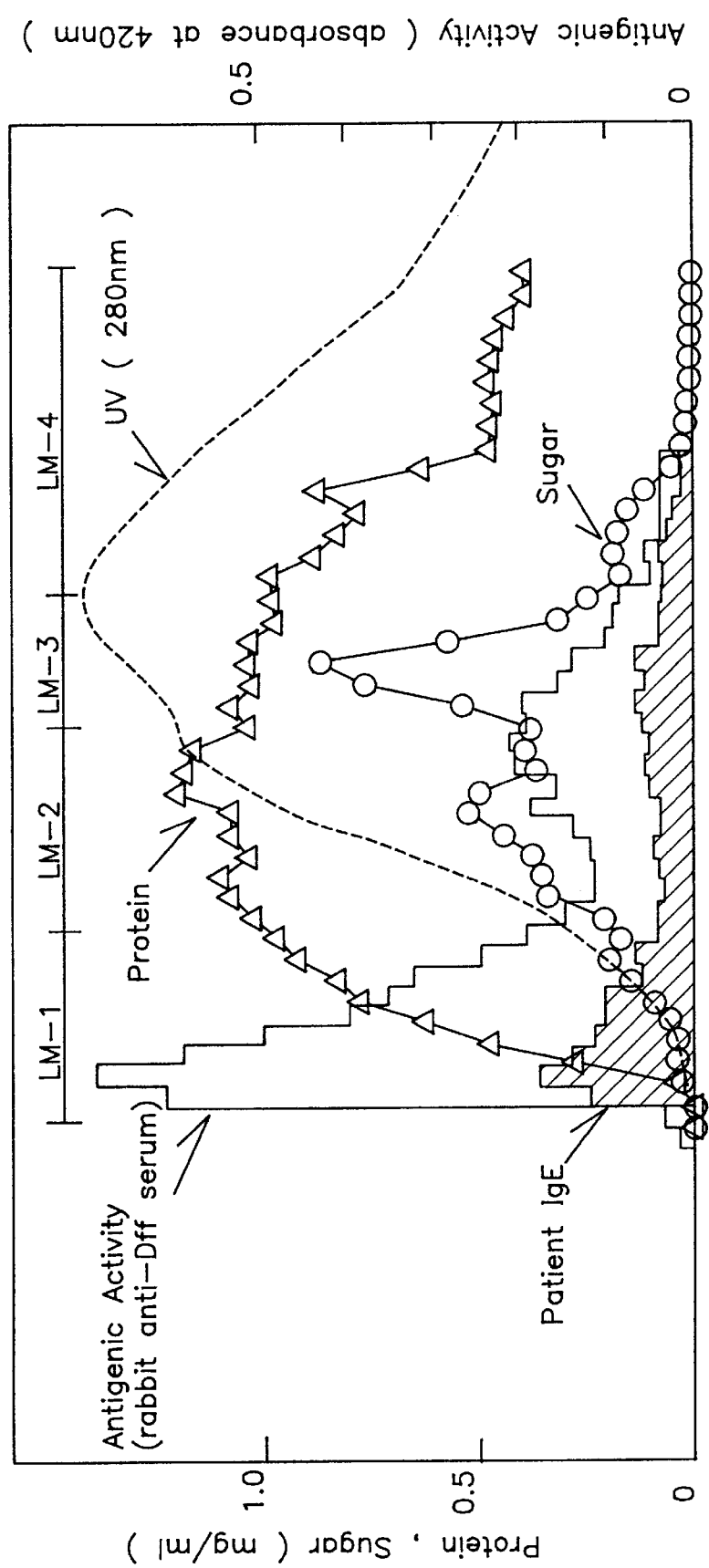
FIG. 8 shows results of gel filtration of a low molecular weight crude mite fecal antigen on Sephadex G25.

260 mg of the low molecular weight crude mite fecal antigen (LM) obtained in Example 1 was fractionated by gel filtration chromatography on Sephadex G25 (produced by Pharmacia Fine Chemical Co.). The results are shown in FIG. 8. Reactivities to rabbit anti-mite fecal serum and to patient serum IgE were detected near the point corresponding to the void volume; peaks appeared in the order of protein, neutral sugar and UV absorbance. The ELISA active fraction near the point corresponding to the void volume, the fraction corresponding to the peak of protein content, the fraction corresponding to the peak of neutral sugar content, and the remaining fraction, respectively named LM-1, LM-2, LM-3 and LM-4, were pooled.

The yield obtained after lyophilization was 47 mg for LM-1, 68 mg for LM-2, 35 mg for LM-3 and 30 mg for LM-4. The fractions LM-1, LM-2, LM-3 and LM-4 were tested for allergen activity by a skin reaction test in mite allergy patiens; LM-1 and LM-2 showed allergen activity.
(b) Gel filtration chromatography of LM-1 on Ultrogel AcA54

LM-1 (360 mg) was further fractionated by gel filtration chromatography on Ultrogel AcA54 (produced by LKB).

Gel filtration was conducted at a sample concentration of 500 mg/20 ml, a buffer concentration of 0.9% (NaCl), a flow rate of 120 ml/hr and a column volume of 1600 ml, while monitoring the fractionation on the basis of leukocyte histamine release activity as well as anti-serum response.

The results are shown in FIG. 3.

Considerable leukocyte histamine release activity was detected in the first half stage of ELISA activity, but the peak of highest activity appeared near the point corresponding to total volume. The high ELISA activity in the first half stage is attributable to response of high molecular weight crude antigen (HM) components which occurred through ultrafiltration in Example 1. The high molecular weight portion with ELISA activity was fractionated and named LM-1A, and the portion with highest histamine release activity was fractionated and named LM-1B. These two fractions were then lyophilized. The yield was 18% (66 mg) for LM-1A and 42% (150 mg) for LM-1B.

LM-1A and LM-1B were tested for allergen activity by a skin reaction test in mite allergy patients; as shown in Table 4, LM-1A and LM-1B were found to have allergen activity.
(c) Fractionation of LM-2 (390 mg) by gel filtration on Ultrogel AcA54

LM-2 was further fractionated by gel filtration on Ultrogel AcA54 (produced by LKB). The gel filtration conditions were the same as those with LM-1. As well as response to antiserum, patient leukocyte histamine release activity was monitored. The results are shown in FIG. 3. The ELISA active portion was named LM-2A and pooled, and the histamine release active portion was named LM-2B and pooled. The yield was 130 mg for LM-2A and 150 mg for LM-2B. LM-2A and LM-2B were tested for allergen activity by a skin reaction test in mite allergy patients; LM-2B alone showed allergen activity (Table 2).

Example 4

Figure 9:
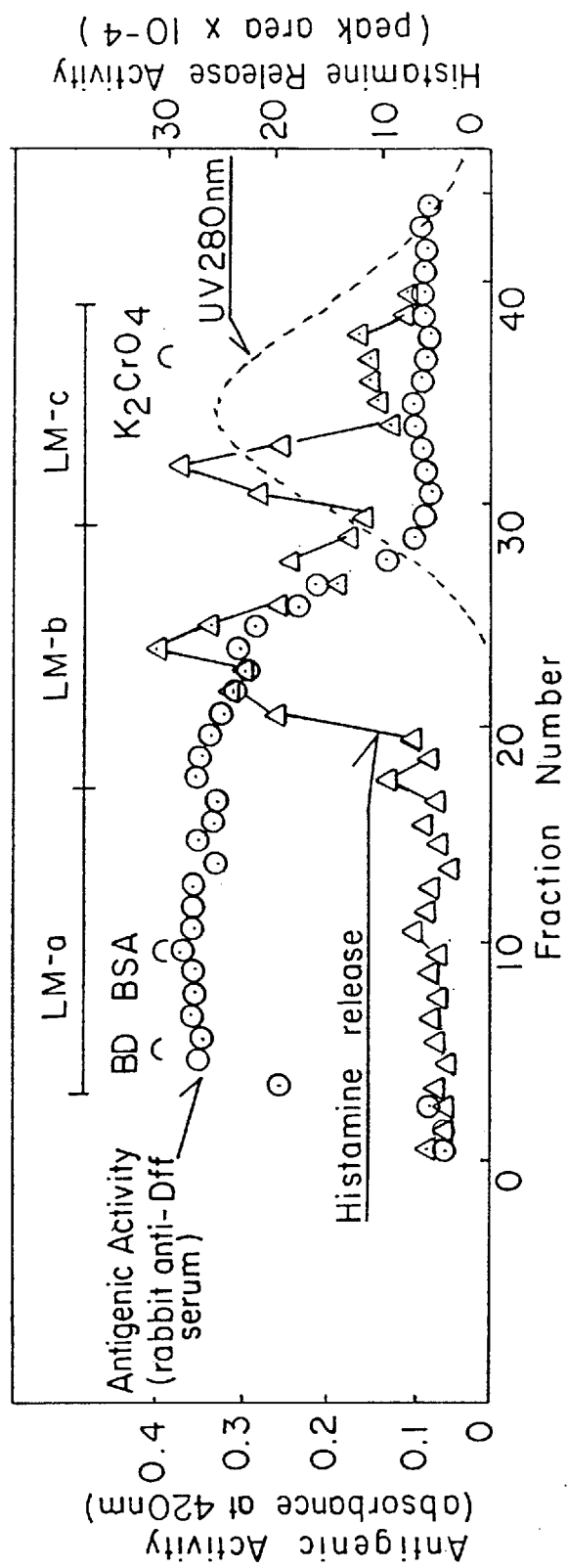
FIG. 9 shows results of gel filtration of a low molecular weight crude mite fecal antigen on Ultrogel AcA54.
Figure 10:
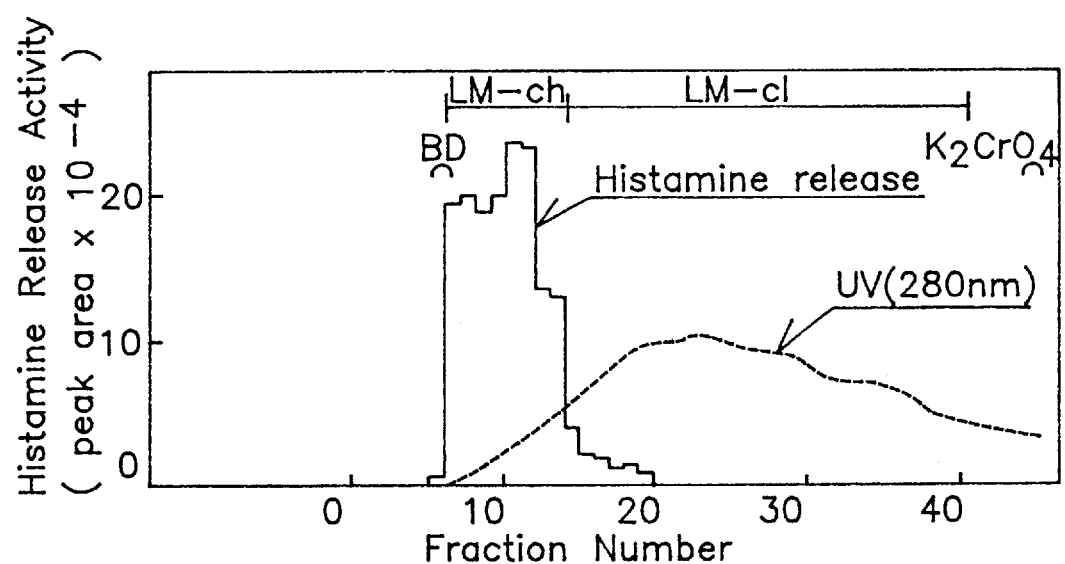
FIG. 10 shows results of gel filtration of LM-c on Sephadex G25.

Purification and compositional analysis of LM-ch:

LM-1B and LM-2B, low molecular allergens which showed strong skin reaction in mite allergy patients, were subjected to compositional analysis. Since these two allergens were very close to each other in both amino acid composition and sugar composition, they were judged to be identical with each other. It was thus decided to purify these two components together. Accordingly, the low molecular weight crude mite fecal antigen (LM) was first fractionated on Ultrogel AcA54; the obtained fractions were assayed for antigenic activity by ELISA using rabbit anti-Dff serum. The obtained low molecular weight fraction (LM-c) was further fractionated using Sephadex G25 to yield a high molecular weight fraction (LM-ch) and a low molecular weight fraction (LM-cl). The results are shown in FIGS. 9 and 10. The gel filtration conditions were the same as in Example 3. LM-ch, corresponding to both LM-1B and LM-2B, was analyzed for amino acid composition and sugar composition. The results are shown in Table 6. The sugar content was determined to be 55% as deduced from the composition. Note that the sugar cotent determined by the phenol sulfuric acid method was about 41%.

TABLE 6

| composition | LM-ch |
|---|---|
| Asx | 67.2 |
| Thr | 28.2 |
| Ser | 32.0 |
| Glx | 113.1 |
| Gly | 85.3 |
| Ala | 32.3 |
| Cys | 2.2 |
| Val | 17.2 |
| Ile | 9.9 |
| Leu | 11.9 |
| Tyr | 0.9 |
| Phe | 4.7 |
| His | 5.4 |
| Arg | 16.6 |
| Lys | 20.8 |
| HexHAc | 64.3 |
| dHex | 17.2 |
| Pen | 252.2 |
| Hex | 216.4 |
| | ($\mu$g/mg) |

Example 5

Estimation of the molecular weight of LM-2B by gel filtration on Sephadex G25:

To estimate the molecular weight of LM-2B, LM-2B was subjected to gel filtration using a Sephadex G25 column, while calibrating with blue dextran (BD), vitamin $B_{12}$ and $K_2CrO_4$. The results are shown in FIG. 11.

Figure 11:
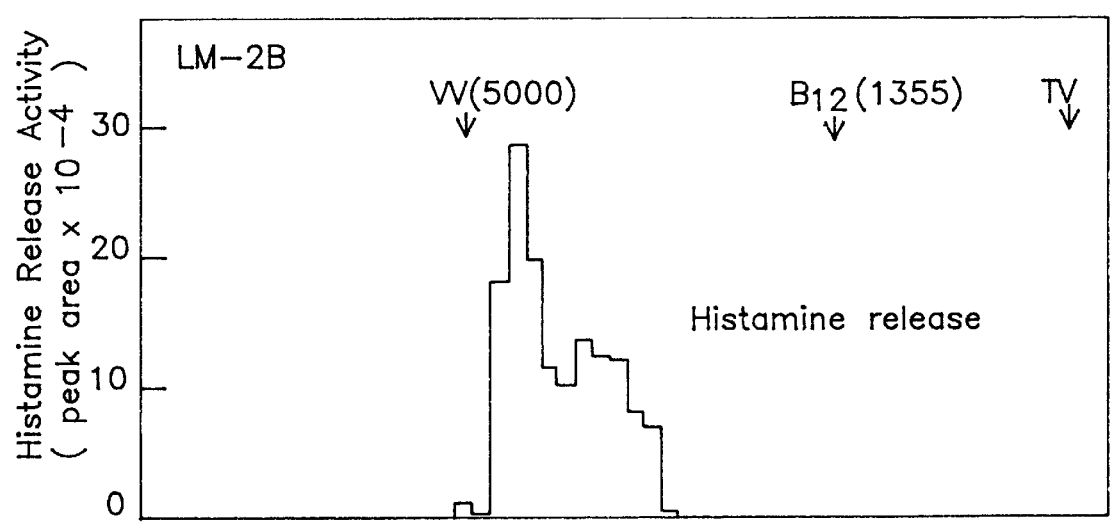
FIG. 11 shows results of gel filtration of LM-2B on Sephadex G25.

The histogram in FIG. 11 indicates histamine release activity on leukocytes in mite allergy patient serum. VV represents the elution position of BD; $B_{12}$ represents the elution position of vitamin $B_{12}$; TV represents the elution position of $K_2CrO_4$. It appears that the leukocyte histamine release activity peak tends to slightly shift toward the low molecular weight side from the void volume peak. Sephadex G25, used as the carrier for gel filtration, has a void molecular weight of 5 k. Based on these facts, the molecular weight of the component of LM-2B showing leukocyte histamine release activity is estimated at 1,500 to 5,000. Also, since LM-ch and LM-2B are considered identical with each other, the molecular weight of LM-ch as well can be estimated at 1,500 to 5,000.

Example 6

Preparation of antigen preparation for hyposensitization therapy:

Dff-1-2-0.1A is dissolved in a 0.9% sodium chloride solution supplemented with 0.5% phenol to reach a concentration of 1 mg/ml; the resulting solution is used as the original solution to prepare an antigen preparation for hyposensitization therapy.

Example 7

Preparation of titration reagent for mite allergy diagnosis:

Dff-1-2-0.1A is dissolved in Hanks' solution to reach a concentration of 1 mg/ml; the resulting solution is used as the original solution to prepare a titration reagent for mite allergy diagnosis.

What is claimed is:

1. A partially purified extract of feces of *Dermatophagoides farinae* containing allergens having the following physicochemical, biochemical and immunological properties:

① being partially purified from fecal extracts of *Dermatophagoides farinae* maintained in culture;

② comprising a glycoprotein containing more than about 40% sugar;

③ having a molecular weight of 1,500 to 5,000 daltons as determined by SEPHADEX G25 gel filtration; and ④ possessing allergen activity.

2. The partially purified extract according to claim 1, which has the following amino acid composition and sugar composition:

Amino acids, $\mu$g/mg: Asx 67.2, Thr 28.2, Ser 32.0, Glx 113.1, Gly 85.3, Ala 32.3, Cys 2.2, Val 17.2, Ile 9.9, Leu 11.9, Tyr 0.9, Phe 4.7, His 5.4, Arg 16.6, Lys 20.8:

Sugar, $\mu$g/mg: HexHAc 64.3, dHex 17.2, Pen 252.2, Hex 216.4.

3. A process for producing a partially purified extract of feces of *Dermatophagoides farinae* containing allergens comprising:

(a) extracting feces of *Dermatophagoides farinae* maintained in culture with a saturated sodium chloride solution and/or a buffer having a moderate ionic strength;

(b) isolating a glycoprotein fraction from the extract obtained from step (a);

(c) fractionating the glycoprotein fraction obtained in step (b); and (d) isolating a fraction comprising allergens having the following physicochemical, biochemical and immunological properties;

① comprising a glycoprotein containing more than about 40% sugar;

② having a molecular weight of 1,500 to 5,000 daltons as determined by SEPHADEX G25 gel filtration; and ③ possessing allergen activity.

4. The process according to claim 3, wherein extracting step (a) is conducted by treatment with a saturated sodium chloride solution and a phosphate buffer.

5. The process according to claim 3, wherein fractionating step (c) is conducted by gel filtration chromatography.

6. A pharmaceutical composition for the treatment of mite allergic diseases which comprises as the active ingredient a pharmaceutically effective amount of the extract according to claim 1 or claim 2 and at least one pharmaceutically acceptable carrier or diluent.

7. A method of treatment of mite allergic diseases which comprises administering a pharmaceutically effective amount of the extract according to claim 1 or claim 2 to a subject.

8. The method of treatment for mite allergic diseases according to claim 7, which is a hyposensitization therapy.

9. A diagnostic composition for mite allergic diseases which comprises as the active ingredient a diagnostically effective amount of the extract according to claim 1 or claim 2.

10. The process according to claim 4, wherein fractionating step (c) is conducted by gel filtration chromatography.

\* \* \* \* \*